(12) United States Patent
Jolly et al.

(10) Patent No.: US 10,335,037 B2
(45) Date of Patent: Jul. 2, 2019

(54) GLOBAL LONGITUDINAL STRAIN FROM CINE MAGNETIC RESONANCE IMAGES

(71) Applicant: Siemens Healthcare GmbH, Erlangen (DE)

(72) Inventors: Marie-Pierre Jolly, Hillsborough, NJ (US); Xiaoguang Lu, West Windsor, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 133 days.

(21) Appl. No.: 15/791,680

(22) Filed: Oct. 24, 2017

(65) Prior Publication Data

US 2019/0117073 A1 Apr. 25, 2019

(51) Int. Cl.
*A61B 5/00* (2006.01)
*A61B 5/055* (2006.01)
*G06T 7/13* (2017.01)

(52) U.S. Cl.
CPC ............ *A61B 5/0044* (2013.01); *A61B 5/055* (2013.01); *G06T 7/13* (2017.01);
(Continued)

(58) Field of Classification Search
CPC ......... A61B 5/0044; A61B 5/055; G06T 7/13; G06T 2207/30048; G06T 2207/10088; G06T 2207/20164; G06K 2209/051
(Continued)

(56) References Cited

U.S. PATENT DOCUMENTS

| | | | |
|---|---|---|---|
| 6,771,803 B1 * | 8/2004 | Turek | G06T 7/12 382/131 |
| 7,813,537 B2 * | 10/2010 | Epstein | G06T 7/215 348/125 |

(Continued)

FOREIGN PATENT DOCUMENTS

| | | | | |
|---|---|---|---|---|
| DE | 102005002949.3 | * | 1/2005 | ............... A61B 6/00 |
| WO | WO 2012/020211 | * | 2/2012 | ............... G06T 7/00 |

OTHER PUBLICATIONS

Self-Adaptive Masking Method for Automatic Shape Recognition and Motion Correction of Thallium-201 Myocardial Perfusion SPECT Imaging Dong et al. Dept. of Medicine East Carolina Univ. Greensville, NC pp. 1-6; Jan. 2018.*

(Continued)

*Primary Examiner* — Jerome Grant, II (57) ABSTRACT

A method for computing global longitudinal strain from cine magnetic resonance (MR) images includes automatically detecting landmark points in each MR long axis image frame included in a cine MR image sequence. A deformation field is determined between every pair of frames based on the landmark points. Myocardial pixels in the frames are labeled using a deep learning framework to yield myocardium masks. These myocardium masks are propagated to each frame using the deformation fields. A polar transformation is performed on each of the masked frames. The contours of the myocardium in each transformed frame are computed using a shortest path algorithm. Next, longitudinal strain is calculated at every pixel in the myocardium for the polar frames using the contours of the myocardium. Then, global longitudinal strain is computed by averaging the longitudinal strain at every pixel in the myocardium of the transformed frames.

19 Claims, 6 Drawing Sheets

(52) U.S. Cl.
CPC .................. *G06K 2209/051* (2013.01); *G06T 2207/10088* (2013.01); *G06T 2207/20164* (2013.01); *G06T 2207/30048* (2013.01)

(58) Field of Classification Search
USPC ........................................................ 382/131
See application file for complete search history.

(56) References Cited

U.S. PATENT DOCUMENTS

| | | | |
|---|---|---|---|
| 8,218,849 B2 | 7/2012 | Lu et al. | |
| 8,494,236 B2 | 7/2013 | Jolly et al. | |
| 8,577,177 B2 | 11/2013 | Guetter et al. | |
| 2008/0015428 A1* | 1/2008 | Epstein | G06T 7/215 |
| | | | 600/410 |
| 2014/0313196 A1* | 10/2014 | Mistretta | G06T 11/008 |
| | | | 345/424 |
| 2017/0065242 A1* | 3/2017 | Chirvasa | A61B 5/055 |

OTHER PUBLICATIONS

Automiatic Segmentation and Cariopathy Classification in Cardiac MRI Images Based on Deep Neural Networks; Chang et al.; School of Eng. Xidian Univ.; IEEE; Jan. 2018 pp. 2010-2014.*
Pipeline for the Wauntification of Cardiac Strain ased on Optical Flow using 4D Ultrasound Data; Loraskul et al. Dept of Biomedical Eng. Columbia University; IEEE; Jan. 2010; pp. 1-2.*

* cited by examiner

GLOBAL LONGITUDINAL STRAIN FROM CINE MAGNETIC RESONANCE IMAGES

This invention was partially made with government support under grant RO1CA167821-01 awarded by National Institute of Health and National Cancer Institute. The government has certain rights in the invention.

TECHNOLOGY FIELD

The present invention relates generally to methods, systems, and apparatuses for determining global longitudinal strain from cine magnetic resonance images. The techniques described herein may be applied to, for example, quantify and visualize global left ventricular (LV) or right ventricular (RV) function.

BACKGROUND

Cardiac function is typically assessed by measuring ejection fraction. This can be done using echocardiography or magnetic resonance (MR) imaging. However, it has been shown that myocardial strain is an early indicator of cardiac abnormality. The term "myocardial strain" (or simply "strain") as used here refers to deformation (e.g., shortening, thickening and/or lengthening) of the myocardium. As is generally known in the art, myocardial strain is a measure of regional left ventricle function.

There are many conventional ways to measure strain using MR images. The most popular approach uses a special pulse sequence to create a dark grid (tags) in the myocardium that deforms with the myocardium. Tags are tracked during the cardiac cycle and strain can be calculated. However, tagged MR generally results in poor spatial resolution. Another technique, displacement encoding with stimulated echoes (DENSE), directly measures a 3D displacement at every pixel in the image, but the acquisition time is very slow. Other conventional techniques such as strain encoding (SENC) offer faster acquisition time but are limited to through plan strain.

SUMMARY

Embodiments of the present invention address and overcome one or more of the above shortcomings and drawbacks, by providing methods, systems, and apparatuses related to measuring global longitudinal strain from cine MR images. The advantage of measuring strain directly from cine images is that cine images are part of the routine exam since they are used to calculate ejection fraction. Thus, by tracking deformations accurately over the cardiac cycle, strain can be calculated directly on cine images. Radial and circumferential strain can be calculated automatically using the automatic segmentation algorithm of short axis cine images. To calculate longitudinal strain automatically, the left ventricle is also automatically segmented in long axis images.

According to some embodiments, a method for computing global longitudinal strain from cine magnetic resonance (MR) images includes receiving a cine MR image sequence comprising a series of long axis image frames of a subject's heart and automatically detecting a plurality of landmark points in each MR long axis image frame. A deformation field is determined between every pair of long axis image frames based on the plurality of landmark points. Myocardial pixels in one or more of the long axis image frames are labeled using a deep learning framework to yield one or more myocardium masks. These myocardium masks are propagated to each long axis image frame using the deformation field between each pair of long axis image frames to yield a plurality of masked long axis images. A polar transformation is performed on each of the masked long axis image frames to yield a plurality of polar long axis images. The contours of the myocardium in each polar long axis image frame are computed using a shortest path algorithm. Next, longitudinal strain is calculated at every pixel in the myocardium for the polar long axis image frames using the contours of the myocardium. Then, global longitudinal strain is computed by averaging the longitudinal strain at every pixel in the myocardium of the polar long axis image frames. In some embodiments, the method further includes presenting a visualization of the global longitudinal strain (e.g., a global longitudinal strain polar map).

In some embodiments of the aforementioned method the plurality of landmark points comprise mitral valve and apical landmark points. The deformation field for each pair of long axis image frames may be determined by aligning the pair of long axis image frames using the mitral valve and the apical landmark points. In one embodiment, this alignment is performed using an inverse consistent deformable registration.

In some embodiments of the aforementioned method, the myocardial pixels in each long axis image frame are labelled by applying a deep convolutional encoder-decoder neural network to classify each pixel in the long axis image frames as myocardium or background.

In some embodiments of the aforementioned method, the contours of the myocardium in each polar long axis image frame are computed by first calculating a gradient of the myocardium mask of the polar long axis image frame. The gradient of the myocardium mask is then converted to polar space and the shortest path algorithm is applied to compute a shortest path with minimum energy in the polar long axis image frame. Energy in this context is defined as the inverse of the gradient. The contours of the myocardium may then be recovered based on the shortest path in the polar long axis image frame. In one embodiment, the shortest path algorithm is Dijkstra's algorithm.

According to another aspect of the present invention, an article of manufacture for computing global longitudinal strain from cine MR images comprises a non-transitory, tangible computer-readable medium holding computer-executable instructions for performing the aforementioned method, with or without the various additional features discussed above.

According to another aspect of the present invention, a method for segmenting myocardium from cine MR images includes receiving a cine MR image sequence comprising a series of long axis image frames of a subject's heart. A deformation field is determined between every pair of long axis image frames based on mitral valve and apical landmark points in each image frame. One or more myocardium masks are generated by applying a deep convolutional encoder-decoder neural network to classify each pixel in the long axis image frames as myocardium or background. These myocardium masks are propagated to each long axis image frame using the deformation field between each pair of long axis image frames to yield a plurality of masked long axis images. A polar transformation is performed on each of the masked long axis image frames to yield a plurality of polar long axis images. The contours of the myocardium in each polar long axis image frame may then be computed using a shortest path algorithm.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to determining global longitudinal strain from cine magnetic resonance images. Briefly, the technology described herein is performed as follows. Landmarks are automatically detected in the long axis images included in a cine MR sequence. A deformation field is calculated based on the landmarks and a myocardial mask is generated for each frame in the sequence. A polar transformation is then applied to the masked images and shortest path contour recovery is performed in all frames. Finally, based on the contours, strain in the long axis and global longitudinal strain are calculated.

Figure 1:
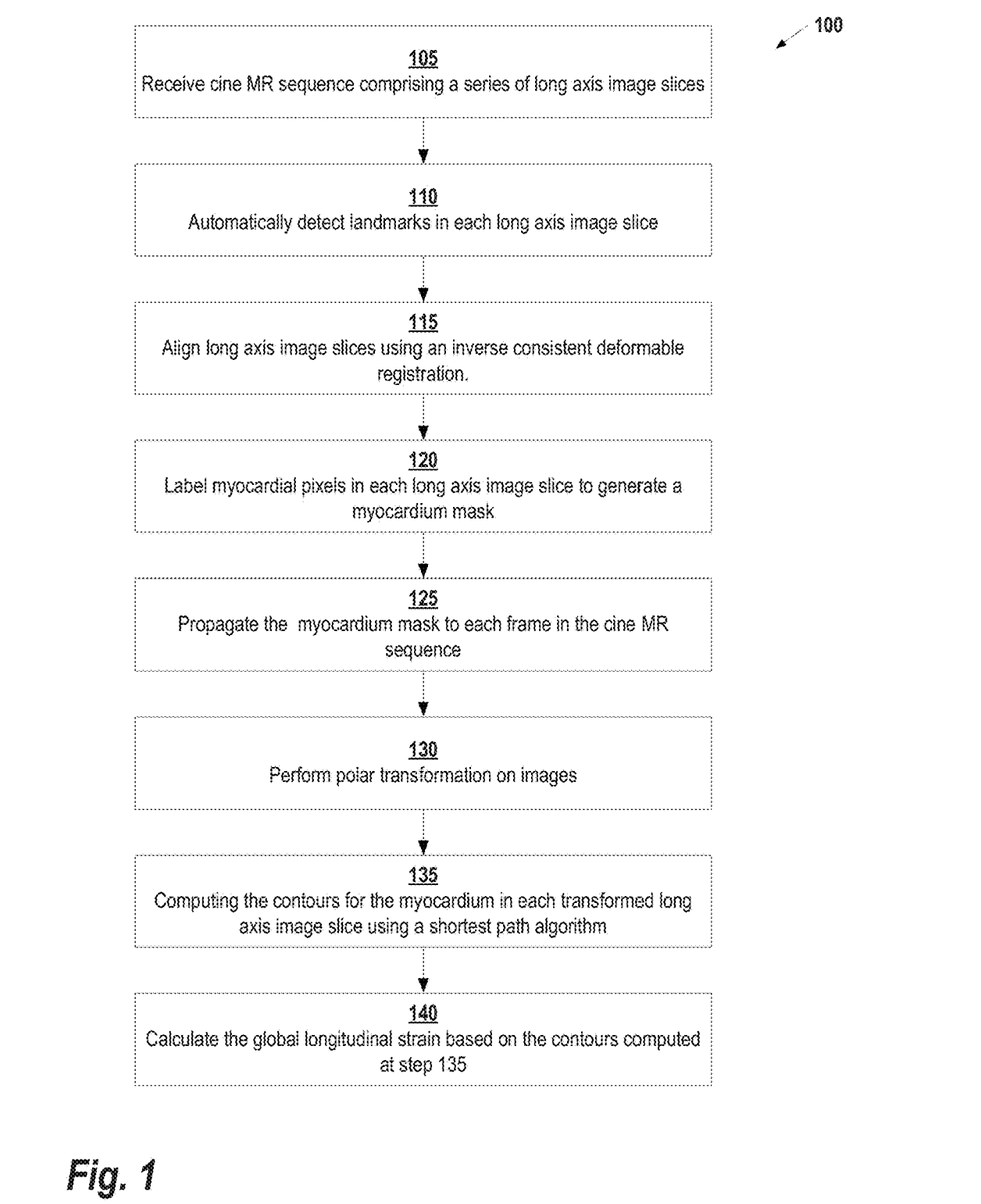
FIG. 1 illustrates an example method for calculating global longitudinal strain from cine magnetic resonance images, according to some embodiments.

FIG. 1 illustrates an example method 100 for calculating global longitudinal strain from cine magnetic resonance images, according to some embodiments. This method may be applied, for example, by a computing system such as illustrated below in FIG. 6. Starting at step 105, a cine MR sequence comprising a series of MR long axis image frames is received by a computing system performing the method 100. Each MR long axis frame is a 2D MR image of at least a cardiac region of a patient. In some embodiments, the computing system is connected, either directly or indirectly over one or more networks to the MR scanner device. In these embodiments, each cine MR sequence can be received directly from an MR scanning device as it acquired or soon thereafter. In other embodiments, the computing system loads cine MR sequences that have been previously stored, for example, on a memory or storage of a computer system or another computer readable medium.

Continuing with reference to FIG. 1, at step 110, landmarks in each long axis image frame are automatically detected by the computing system. These landmarks may comprise, for example, the mitral valve and apical landmark points in the long axis image frame. In general, any suitable technique known in the art may be used to detect the relevant landmarks in the image. One example detection method is described in U.S. Pat. No. 8,218,849, issued Jul. 10, 2012 and entitled "Method and system for automatic landmark detection using discriminative joint context," the entirety of which is incorporated herein by reference. Briefly, a machine learning technique is used to learn the image context around the individual landmark points as well as around the group of landmarks. Then, marginal space learning is used to recover the landmarks scale, orientation, and translation in a new image.

Next at step 115, the long axis image frames are aligned to one another using an inverse consistent deformable registration. This results in a deformation field (forward and backward) between every pair of images in the series. One example method for performing deformable registration is described in U.S. Pat. No. 8,577,177, issued Nov. 5, 2013 and entitled "Symmetric and inverse-consistent deformable registration,"

Following registration, the myocardial pixels in each long axis image frame are labeled at step 120. In some embodiments, this labelling is performed by a deep learning framework. Such a deep learning framework may include one or more machine learning models (e.g., neural networks) trained based on a set of long axis images with corresponding labeling data. In one embodiment, at step 120 a deep convolutional encoder-decoder neural network is applied to classify each pixel into one of the two categories, myocardium or background. The end result of the labeling performed at step 120 is the generation of a probabilistic mask for the myocardium. This mask sets the pixel values in an image to zero, or some other "background" value if no portion of the myocardium is present in that pixel.

After the myocardium mask is computed, it is propagated to each frame in the image sequence at step 125. The myocardium mask is not perfect and does not necessarily cover all the myocardium pixels. Since the goal is to recover the myocardium in all frames, the algorithm takes advantage of the different responses from the deep learning performed at step 120 at different frames. A subset of the frames is selected on which deep learning is applied to recover the myocardial mask. In some embodiments, the frames are randomly selected, while in other embodiments the frames are selected based on other factors such as, for example, where in the cardiac cycle the frame was acquired. Once generated, the mask is propagated to the other frames using the deformation fields recovered from step 115. At each frame, there are now multiple deformed masks coming from different initial frames. These masks are averaged to produce a weighted mask at every frame.

Figure 2:
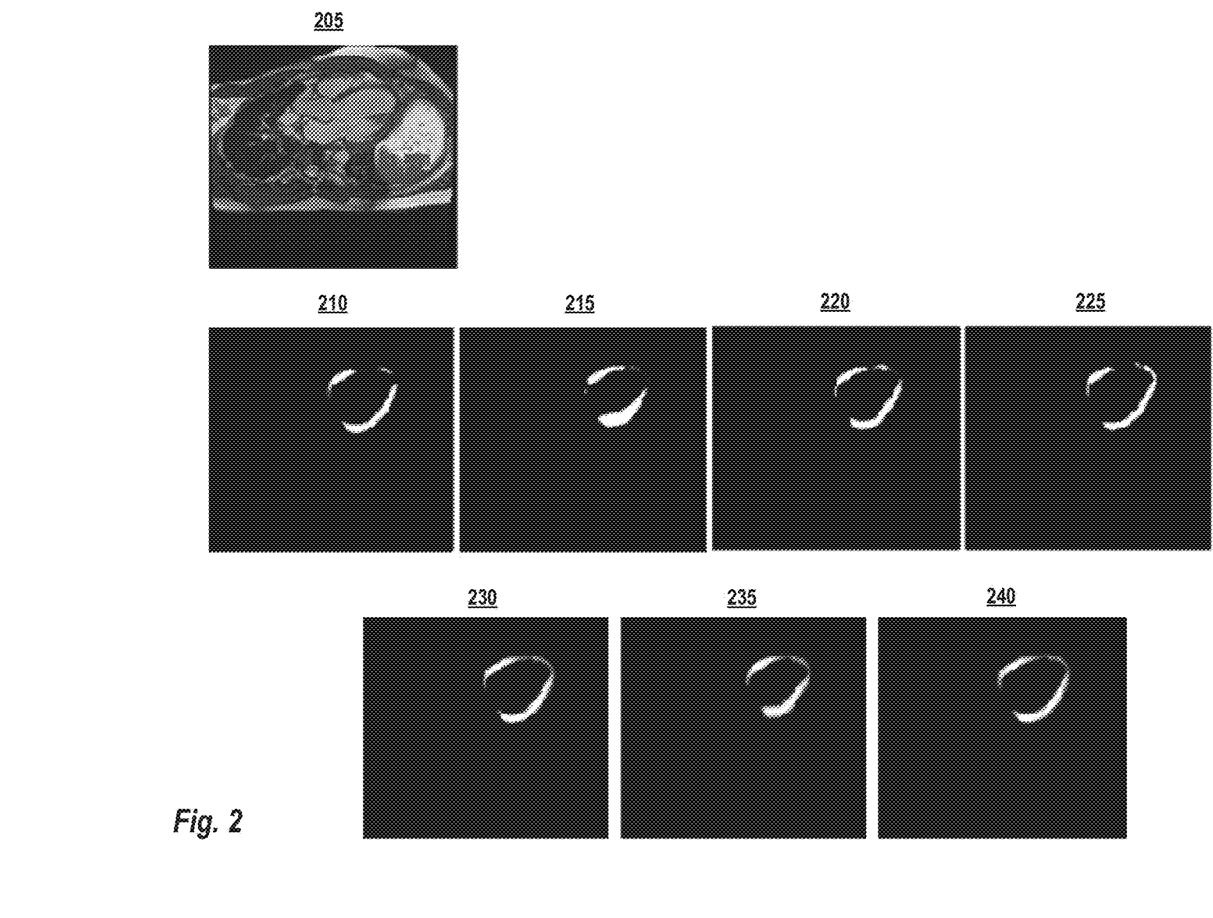
FIG. 2 illustrates a method of generating a myocardium mask, according to some embodiments.

FIG. 2 shows an example of the process performed at steps 120 and 125. Based on an input frame 205, deep learning probability is calculated for every 4 frames in the image sequence (i.e., frames 210-225). Then, masks are generated at every frame through averaging as shown in frames 230-240.

Figure 3:
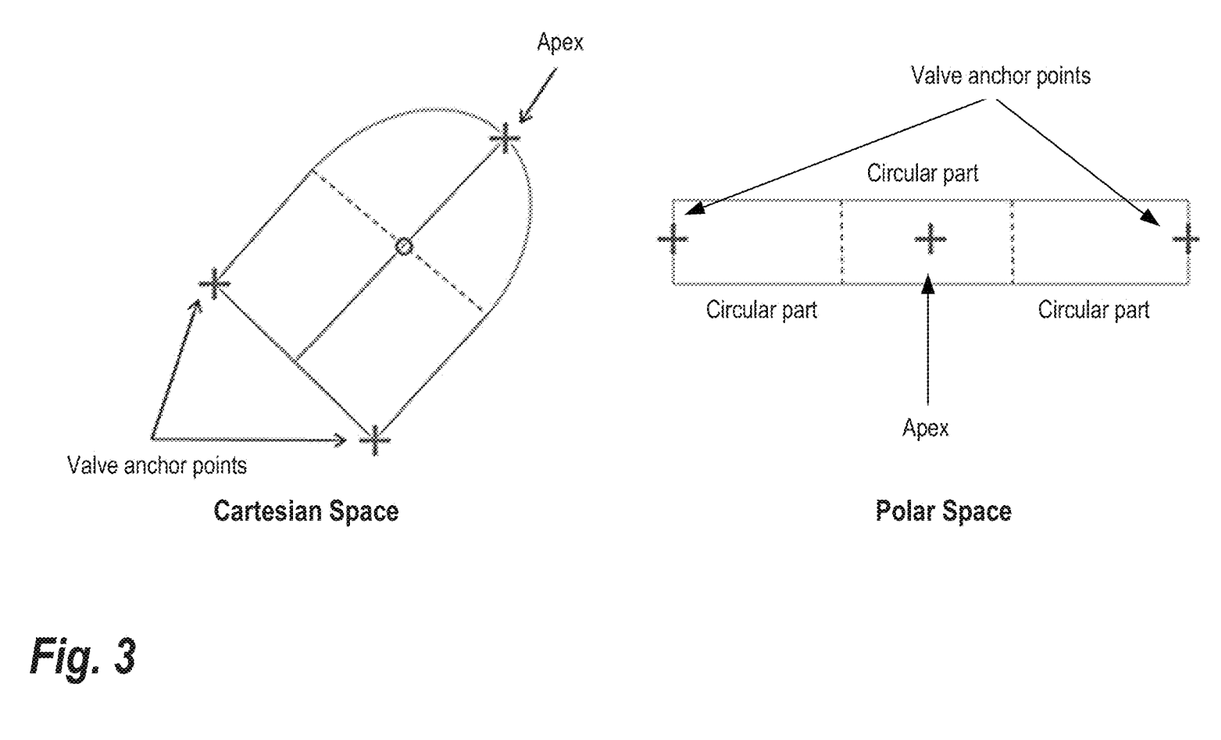
FIG. 3 shows a combination of cylindrical and polar transformation that may be applied to the left ventricle in long axis images, according to some embodiments.

Returning to FIG. 1, at step 130, a cylindrical/polar transformation is performed on the images. As described below, the final recovery of the contours is performed using the gradients of the mask images and applying a shortest path algorithm. However, in order to not be biased towards small contours, the contour recovery is done in the polar coordinates rather than in the original image. Since the shape of the left ventricle in long axis images is not really round, it is more appropriate to use a combination of cylindrical and polar transformation as depicted in FIG. 3. The left hand side of FIG. 3 shows the apex and valve anchor points in Cartesian space, while the right hand side depicts the points in polar space. In general, standard cylindrical and polar transformations may be applied to transform the images. The center of the transformation is along the centerline for the cylindrical part and at the center of the bottom circle for the polar part.

Figure 4:
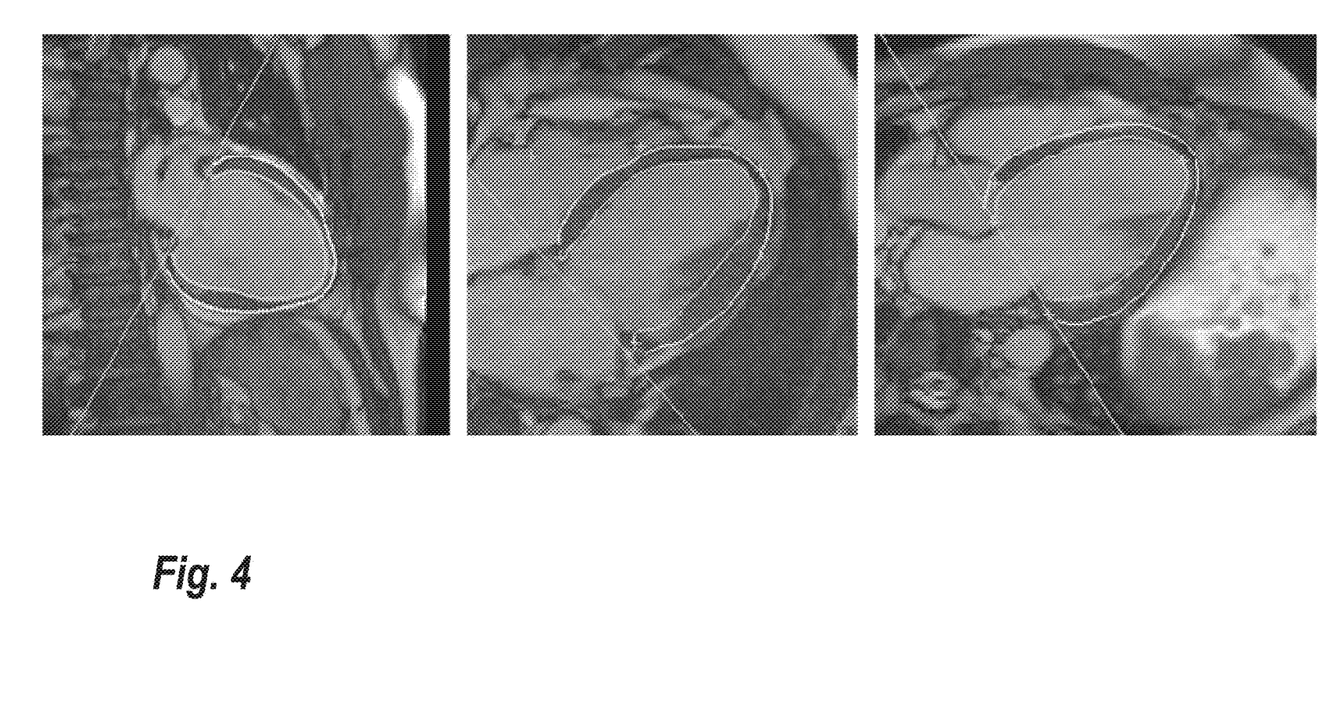
FIG. 4 shows examples of myocardium segmentation in long axis images, according to some embodiments.

Next, at step 135, the computing system computes the contours for the myocardium in each transformed long axis image frame using a shortest path algorithm. An example technique for performing this recovery is described in U.S. Pat. No. 8,494,236, issued Jul. 23, 2013 and entitled "System and method for cardiac segmentation in MR-cine data using inverse consistent non-rigid registration," the entirety of which is incorporated herein by reference. The gradient of the myocardium mask is calculated and converted to cylindrical/polar space. Then, the shortest path with minimum energy is recovered in the polar recovered space using Dijkstra's algorithm, where the energy is defined as the inverse of the gradient. The contour is then propagated to the other frame. This process is repeated for all frames. The final set of contours for the frame is chosen as the set of contours with largest gradient. FIG. 4 shows examples of myocardium segmentation in long axis images.

Figure 5:
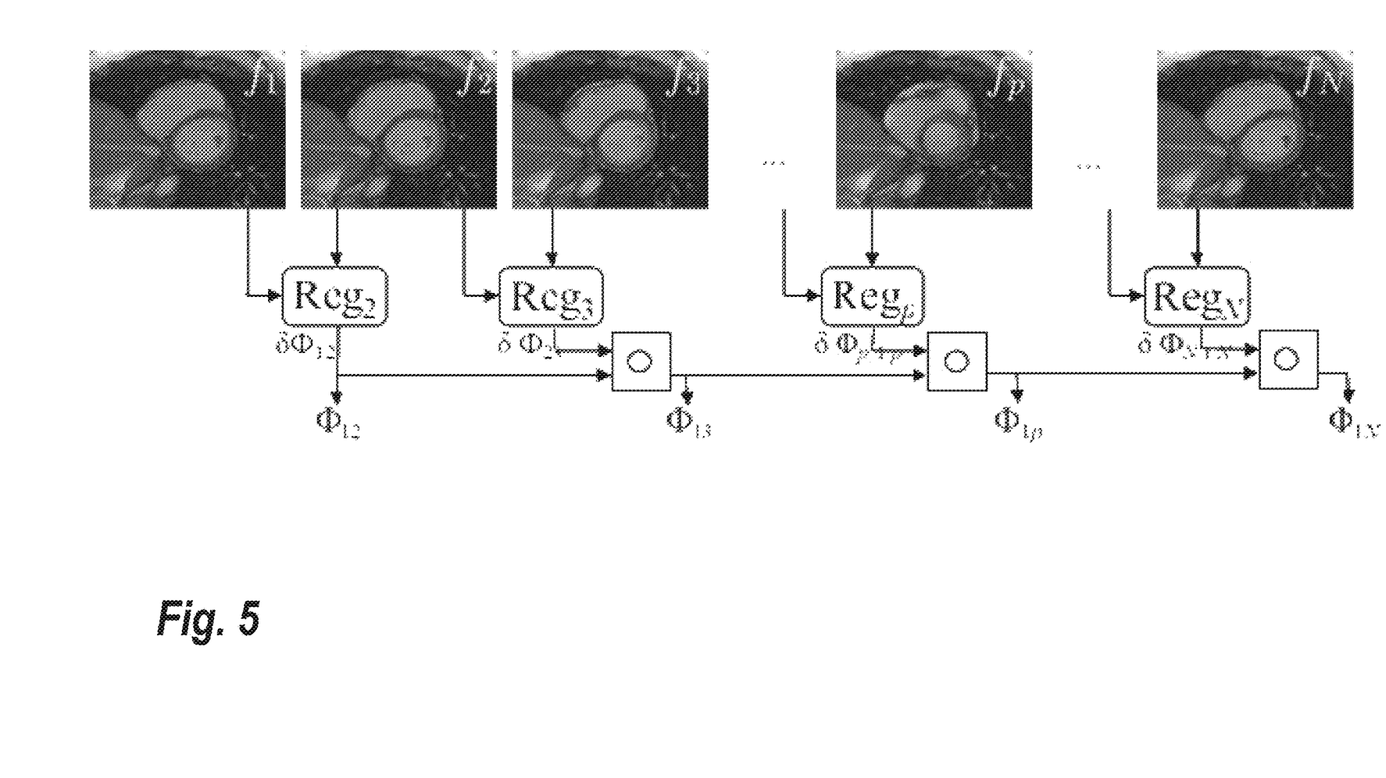
FIG. 5 shows how three deformation fields are calculated at every pixel in the images using the consecutive registration process, according to some embodiments.

At step 140, the global longitudinal strain is calculated based on the contours computed at step 135. As illustrated in FIG. 5, the forward deformation field and the backward deformation field are calculated at every pixel in the images using the consecutive registration process. Therefore, it is possible to calculate the strain at every pixel inside the myocardium as follows. The displacement $\Delta_{p,p+1}(x,y)$ between frame p and the next frame at position (x,y) is computed as:

$$\Delta_{p,p+1}(x,y) = \Phi_{1,p+1}(\Phi_{1,p}^{-1}(x,y))) - (x,y)$$

The total displacement $\Delta_{1,p}(x,y)$ since the first frame is computed as:

$$\Delta_{1,p}(x,y) = \Omega_{1,p}(x,y)$$

The displacements are expressed in millimeters (mm) by multiplying each coordinate by the pixel dimensions. They are projected onto the radial and circumferential/longitudinal direction simply by taking the dot product of the displacement vector with the radial and circumferential/longitudinal direction at point (x,y).

The velocity between frame p and the next frame at position (x,y) is computed as:

$$v_{p,p+1}(x,y) = \frac{\Delta_{p,p+1}(x,y)}{\Delta T_{p,p+1}}$$

The velocity is expressed in mm/s. The radial and circumferential/longitudinal velocities can also be computed by taking the dot product with the radial and circumferential/longitudinal direction.

The Lagrange strain tensor is defined as $E=0.5(F^T \cdot F - I)$ and can also be expressed in terms of the displacement gradients as follows:

$$E_{ij} = \frac{1}{2}\left(\frac{\partial \Phi_i}{\partial x_j} + \frac{\partial \Phi_j}{\partial x_i} + \sum_k \frac{\partial \Phi_k}{\partial x_j}\frac{\partial \Phi_k}{\partial x_i}\right)$$

with an implied sum over k. The gradient of the deformation fields are computed using a Deriche filter. Then, the strain measurements are defined as:

$$\epsilon_{radial} = E_{00}\cos^2\theta + E_{11}\sin^2\theta + E_{01}\sin\theta\cos\theta$$

$$\epsilon_{circumferential} = E_{00}\sin^2\theta + E_{11}\cos^2\theta - E_{01}\sin\theta\cos\theta$$

$$\gamma_{sheer} = 2(E_{11} - E_{00})\sin\theta\cos\theta + E_{01}(\cos^2\theta - \sin^2\theta)$$

The global longitudinal strain may then be computed by averaging the longitudinal strain at every pixel in the myocardium for the long axis frames. Once calculated global longitudinal strain values may be used to present a visualization such as a global longitudinal strain polar map.

Figure 6:
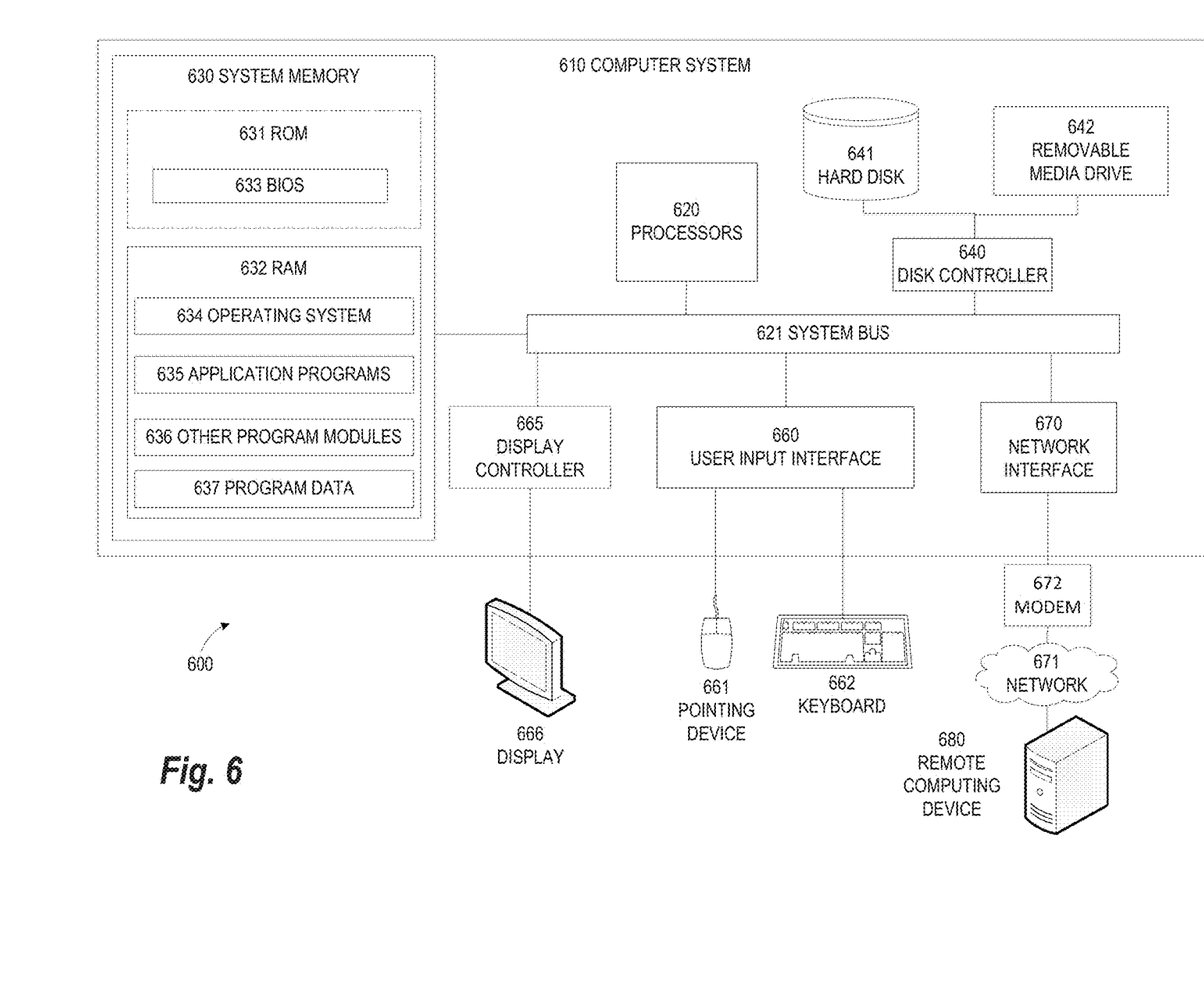
FIG. 6 illustrates an exemplary computing environment within which embodiments of the invention may be implemented.

FIG. 6 illustrates an exemplary computing environment 600 within which embodiments of the invention may be implemented. For example, this computing environment 600 may be used to implement the process 100 described in FIG. 1. In some embodiments, the computing environment 600 may be used to implement one or more of the components illustrated in the system 600 of FIG. 6. The computing environment 600 may include computer system 610, which is one example of a computing system upon which embodiments of the invention may be implemented. Computers and computing environments, such as computer system 610 and computing environment 600, are known to those of skill in the art and thus are described briefly here.

As shown in FIG. 6, the computer system 610 may include a communication mechanism such as a bus 621 or other communication mechanism for communicating information within the computer system 610. The computer system 610 further includes one or more processors 620 coupled with the bus 621 for processing the information. The processors 620 may include one or more central processing units (CPUs), graphical processing units (GPUs), or any other processor known in the art.

The computer system 610 also includes a system memory 630 coupled to the bus 621 for storing information and instructions to be executed by processors 620. The system memory 630 may include computer readable storage media in the form of volatile and/or nonvolatile memory, such as read only memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device (s) (e.g., programmable ROM, erasable PROM, and electrically erasable PROM). In addition, the system memory 630 may be used for storing temporary variables or other intermediate information during the execution of instructions by the processors 620. A basic input/output system (BIOS) 633 containing the basic routines that help to transfer information between elements within computer system 610, such as during start-up, may be stored in ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the bus 621 to control one or more storage devices for storing information and instructions, such as a hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the bus 621 to control a display 666, such as a cathode ray tube (CRT) or liquid crystal display (LCD), for displaying information to a computer user. The computer system includes an input interface 660 and one or more input devices, such as a keyboard 662 and a pointing device 661, for interacting with a computer user and providing information to the processor 620. The pointing device 661, for example, may be a mouse, a trackball, or a pointing stick for communicating direction information and command selections to the processor 620 and for controlling cursor movement on the display 666. The display 666 may provide a touch screen interface which allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a hard disk 641 or a removable media drive 642. The hard disk 641 may contain one or more datastores and data files used by embodiments of the present invention. Datastore contents and data files may be encrypted to improve security. The processors 620 may also be employed in a multi-processing arrangement to execute the one or more sequences of instructions contained in system memory 630. In alternative embodiments, hard-wired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments of the invention and for containing data structures, tables, records, or other data described herein. The term "computer readable medium" as used herein refers to any medium that participates in providing instructions to the processor 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include the computer system 610 operating in a networked environment using logical connections to one or more remote computers, such as remote computer 680. Remote computer 680 may be a personal computer (laptop or desktop), a mobile device, a server, a router, a network PC, a peer device or other common network node, and typically includes many or all of the elements described above relative to computer system 610. When used in a networking environment, computer system 610 may include modem 672 for establishing communications over a network 671, such as the Internet. Modem 672 may be connected to bus 621 via user network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computer 680). The network 671 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 671.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for computing global longitudinal strain from cine magnetic resonance (MR) images, the method comprising:
   receiving a cine MR image sequence comprising a series of long axis image frames of a subject's heart;
   automatically detecting a plurality of landmark points in each MR long axis image frame;
   determining a deformation field between every pair of long axis image frames based on the plurality of landmark points;
   labeling myocardial pixels in one or more of the long axis image frames using a deep learning framework to yield one or more myocardium masks;
   propagating the myocardium masks to each long axis image frame using the deformation field between each pair of long axis image frames to yield a plurality of masked long axis images;
   performing a polar transformation on each of the masked long axis image frames to yield a plurality of polar long axis images;
   computing contours of the myocardium in each polar long axis image frame using a shortest path algorithm;
   calculating longitudinal strain at every pixel in the myocardium for the polar long axis image frames using the contours of the myocardium; and
   computing global longitudinal strain by averaging the longitudinal strain at every pixel in the myocardium of the polar long axis image frames.

2. The method of claim 1, wherein the plurality of landmark points comprise mitral valve and apical landmark points.

3. The method of claim 2, wherein the deformation field for each pair of long axis image frames is determined by aligning the pair of long axis image frames using the mitral valve and the apical landmark points.

4. The method of claim 3, wherein the alignment is performed using an inverse consistent deformable registration.

5. The method of claim 1, wherein the myocardial pixels in each long axis image frame are labelled by applying a deep convolutional encoder-decoder neural network to classify each pixel in the long axis image frames as myocardium or background.

6. The method of claim 1, wherein computing the contours of the myocardium in each polar long axis image frame using the shortest path algorithm comprises:
   calculating a gradient of the myocardium mask of the polar long axis image frame;
   converting the gradient of the myocardium mask to polar space;
   applying the shortest path algorithm to compute a shortest path with minimum energy in the polar long axis image frame, wherein energy is defined as the inverse of the gradient;
   recovering the contours based on the shortest path in the polar long axis image frame.

7. The method of claim 6, wherein the shortest path algorithm is Dijkstra's algorithm.

8. The method of claim 1, further comprising:
   presenting a visualization of the global longitudinal strain.

9. The method of claim 8, wherein the visualization of global longitudinal strain is a global longitudinal strain polar map.

10. An article of manufacture for computing global longitudinal strain from cine MR images, the article of manufacture comprising a non-transitory, tangible computer-readable medium holding computer-executable instructions for performing a method comprising:
    automatically detecting a plurality of landmark points in a plurality of MR long axis image frames included a cine MR image sequence;
    determining a deformation field between every pair of long axis image frames based on a plurality of landmark points in each MR long axis image frame;
    labeling myocardial pixels in one or more of the long axis image frames using a deep learning framework to yield one or more myocardium masks;
    propagating the myocardium masks to each long axis image frame using the deformation field between each pair of long axis image frames to yield a plurality of masked long axis images;
    performing a polar transformation on each of the masked long axis image frames to yield a plurality of polar long axis images;
    computing contours of the myocardium in each polar long axis image frame using a shortest path algorithm;
    calculating longitudinal strain at every pixel in the myocardium for the polar long axis image frames using the contours of the myocardium; and
    computing global longitudinal strain by averaging the longitudinal strain at every pixel in the myocardium of the polar long axis image frames.

11. The apparatus of claim 10, wherein the plurality of landmark points comprise mitral valve and apical landmark points.

12. The apparatus of claim 11, wherein the deformation field each pair of long axis image frames is determined by aligning the pair of long axis image frames using the mitral valve and the apical landmark points.

13. The apparatus of claim 12, wherein the alignment is performed using an inverse consistent deformable registration.

14. The apparatus of claim 10, wherein the myocardial pixels in each long axis image frame are labelled by applying a deep convolutional encoder-decoder neural network to classify each pixel in the long axis image frames as myocardium or background.

15. The apparatus of claim 10, wherein computing the contours of the myocardium in each polar long axis image frame using the shortest path algorithm comprises:
    calculating a gradient of the myocardium mask of the polar long axis image frame;

converting the gradient of the myocardium mask to polar space;

applying the shortest path algorithm to compute a shortest path with minimum energy in the polar long axis image frame, wherein energy is defined as the inverse of the gradient;

recovering the contours based on the shortest path in the polar long axis image frame.

16. The apparatus of claim 15, wherein the shortest path algorithm is Dijkstra's algorithm.

17. The apparatus of claim 10, further comprising:

generating a visualization of the global longitudinal strain.

18. The apparatus of claim 17, wherein the visualization of global longitudinal strain is a global longitudinal strain polar map.

19. A method for segmenting myocardium from cine MR images, the method comprising:

receiving a cine MR image sequence comprising a series of long axis image frames of a subject's heart;

determining a deformation field between every pair of long axis image frames based on mitral valve and apical landmark points in each image frame;

generating one or more myocardium mask by applying a deep convolutional encoder-decoder neural network to classify each pixel in the long axis image frames as myocardium or background;

propagating the myocardium masks to each long axis image frame using the deformation field between each pair of long axis image frames to yield a plurality of masked long axis images;

performing a polar transformation on each of the masked long axis image frames to yield a plurality of polar long axis images; and computing contours of the myocardium in each polar long axis image frame using a shortest path algorithm.

\* \* \* \* \*